United States Patent [19]
Rohdewald

[11] Patent Number: 5,993,867
[45] Date of Patent: Nov. 30, 1999

[54] CAPSULES CONTAINING FREEZE-DRIED, POWDERED GREEN TEA LEAVES

[75] Inventor: Peter Rohdewald, Altenberge, Germany

[73] Assignee: Freeze Dry Foods, GmbH, Greven, Germany

[21] Appl. No.: 08/913,829

[22] PCT Filed: Dec. 27, 1995

[86] PCT No.: PCT/EP95/05149

§ 371 Date: Sep. 4, 1997

§ 102(e) Date: Sep. 4, 1997

[87] PCT Pub. No.: WO97/07685

PCT Pub. Date: Mar. 6, 1997

[30] Foreign Application Priority Data

Aug. 22, 1995 [DE] Germany ............... 195 30 868

[51] Int. Cl.$^6$ .............. A23L 1/216; A23C 1/06; A23F 3/00; A23B 4/03

[52] U.S. Cl. .............. 426/96; 426/384; 426/597; 426/443; 426/518

[58] Field of Search .................... 426/384, 597, 426/443, 518, 96

[56] References Cited

U.S. PATENT DOCUMENTS

H1620 12/1996 Dolan et al. .............. 426/593

FOREIGN PATENT DOCUMENTS 3414767 7/1995 Germany .

OTHER PUBLICATIONS

Database Abstract. An: 89(07):V0027 FSTA for DE 3719991. Inventor: Gehrig, 1988.
D1—Nomura, Takeo, et al. "Antitumor Agents from Tea Leaves of MHC Restriction," Source: JP63267726 A Published Nov. 4, 1988.
D2—"Tea Granule Preparation Freeze Puversie Tea Leaf Below Degree Coating Granule Tea Powder Obtain Water Soluble Coating Gelatin" Source: JP58198246 A Published Nov. 18, 1983.
D3—"Instant Powder Tea Control Age Comprise Dust Late Pick Green Tea Extract Pick Leaf Natural Antioxidant Vitamin E" Source: JP3228646 A Published Oct. 9, 1991.
D4—"Powder Green Tea Encapsulate Water Soluble Material Gelatin" Source: JP870324316 Published Dec. 21, 1987.
D5—"Production of Powdered Green Tea" Source: JP870000325 Published Jan. 5, 1987.
D6—"Powdered Tea Product" Source: CN930112865 Published Dec. 25, 1993.
D8—"Deoxidise Contain Polyphenol Oxidase Polyphenol Powder Vegetable Tissue Potato Tuber Tobacco Leaf Tea Leaf" Source: JP780023209 Published Mar. 1, 1978.
D9—"Tea Preparation Medicine Properties Comprise Pulverise Dry Leaf Form Sort Tea Flour" Source: JP900066026 Published Mar. 16, 1990.

*Primary Examiner*—Anthony J. Weier

[57] ABSTRACT

The invention relates to a process for producing a preparation containing the polyphenols of green tea (*Thea chinensis*) in readily available, unoxidised form, in which fresh green tea leaves are cooled until the activity of the phenol oxidases therein has dropped to at most 1% of the value at normal temperature and at the same time or immediately afterwards the water acting as the reaction medium is removed. Products made by this process are packed in capsules soluble in hot water.

11 Claims, No Drawings

CAPSULES CONTAINING FREEZE-DRIED, POWDERED GREEN TEA LEAVES

The present invention concerns a process for the production of a preparation which contains the polyphenols of green tea (*Thea chinensis*) in readily available, non-oxidised form, which is characterised in that one cools fresh green tea leaves until the activity of the contained phenol oxidases has decreased to at most 1% of the value at normal temperature and simultaneously or immediately thereafter the water effective as reaction medium is removed and products produced according to this process.

It is known that unfermented (green) tea, besides the action as enjoyable material, also displays pharmacological properties which are suitable for the prevention of diseases in that, on the one hand, the anti-oxidative capacity of the human or animal organism is increased and, furthermore, the vascular system, especially the capillary system, is protected.

The anti-oxidative properties of unfermented tea can be attributed to the ability of the polyphenols contained in the leaves of *Thea chinensis*, especially the gallocatechins, to inactivate free radicals. Summaries referring to this are to be found in Lit. 1 of the accompanying bibliography.

The frequently demonstrated inactivating action of unfermented tea with regard to carcinogenic and precarcinogenic substances (Lit. 2) stands in close connection with the binding of free radicals. An anti-bacterial and bactericidal effect of unfermented tea has also been demonstrated (Lit. 3). Finally, a lowering of the plasma cholesterol has also been shown in animal experiments (Lit. 4).

Hitherto, for the utilisation of the polyphenols of tea leaves, various extraction processes have been employed in order to extract as quantitatively as possible the water-soluble components and to produce a water-soluble extract, whereby, as starting materials, not only fermented but also unfermented tea (Lit.5) found use.

The oxidation of value-determining components of tea leaves begins shortly after harvesting by means of phenol oxidases. Furthermore, also after inactivation of the phenol oxidases by heating, an oxidation of the polyphenols takes place. Finally, the fermentation of the tea has the result that the oxidation can be utilised in a controlled manner for the formation of certain aroma materials.

Therefore, the task forming the basis of the invention is to keep intact as far as possible qualitatively as well as quantitatively the total palette of the component materials of fresh green tea leaves but, at the same time, to make them readily accessible for the user. In particular, it is an object of the invention to bring the contained component materials qualitatively and quantitatively intact into a form which offers the user the possibility of taking these component materials of the tea leaves either in the form of an infusion or to take the tea leaves themselves as such in dry form.

According to the invention, this task is solved in that one first minimises the activity of the phenol oxidases of the fresh green tea leaves by cooling and simultaneously or immediately thereafter prevents the enzymatic reaction of the polyphenols by phenol oxidases by removal of the water reaction medium. For this purpose, especially the fresh green tea leaves are cooled until the activity of the phenol oxidases contained therein has decreased to at most 1% of the activity of the fresh green tea leaves at ambient temperature and simultaneously or immediately thereafter the water effective as reaction medium is removed.

Cooling and water removal are preferably carried out simultaneously by by lyophilisation (freeze drying). The freeze-dried, unfermented tea leaves are thereafter finely pondered in non-oxidising atmosphere and subsequently packed, again with oxygen exclusion. Nitrogen and/or noble gas atmosphere is preferably used as non-oxidising atmosphere. However, other atmosphere compositions can also be used provided that they exert no oxidising action on the polyphenols.

The freeze-dried, unfermented tea leaves produced according to the process of the invention in finely powdered form can be packed directly or be previously subjected to a treatment for the removal of caffeine. The caffeine removal expediently takes place by extraction with supercritical $CO_2$, thus under conditions which, with regard to pressure and temperature, lie above the critical limit. Processes for the extraction of vegetable materials with supercritical $CO_2$ are known to the expert and do not therefore here require more detailed explanation. If such a caffeine extraction is carried out, then, before the packing, one allows any residues of extraction agent simply to vaporise into the atmosphere and then carries out the packing in the same way as in the case of powder not subjected to $CO_2$ extraction.

The packing preferably takes place into bio-compatible capsules completely soluble in hot water under the above-mentioned conditions. Hard capsules of gelatine or soft gelatine capsules have proved to be especially suitable. However, in principle, for this embodimental form of the invention, any capsule material is usable which dissolves without residues in water at 100° C. and is pharmaceutically compatible.

However, the pulverised tea leaf preparations obtained according to the invention can also be packed in other forms, so long as non-oxidising and water-free conditions can be maintained. Thus, for example, there comes into consideration the packing into liposomes with the use of water-free methods and protective gas atmospheres. Suitable methods of production for such liposome preparations are known to the expert. However, because of the simple production and versatile possibilities of use, the capsules obtainable according to the invention are preferred and are, therefore, per se a subject of the invention. The capsules according to the invention bring about, on the one hand, a protection against the oxidation of the tea powder but, on the other hand, also serve the purpose of offering to the user a flavour-neutral or flavoured alternative, adjusted as desired, for taking the tea powder produced according to the invention as suspension in hot water.

Anti-oxidants, vitamins and trace elements can additionally be added to the capsules according to the invention. Furthermore, taste-correcting water-free aromas, especially vegetable components, can be added. Known dried plants preferably used for the production of tea, such as e.g. peppermint, mallow, camomile and the like, are thereby preferred.

As nutrition-supplementing agents, capsules according to the invention with a content of 100 to 400 mg of the finely-powdered, unfermented green tea leaves obtainable according to the invention are taken 1 to 3 times daily, either as aqueous suspension or in capsule form. If the longer lasting and slowly commencing invigorating action of the tea leaves is to stand in the foreground, then capsules are filled with 400 to 800 mg of the tea leaf material obtained according to the invention which, as required, are taken either as aqueous suspension or as capsules.

The following Examples explain the invention.

EXAMPLE 1

Freshly plucked leaves of the tea bush are transported in a cooled wagon to the freeze drying and are deep frozen and freeze dried on the same day. The freeze-dried leaves are powdered with nitrogen gassing. This powder is either immediately packed, while gassing with nitrogen, into tightly closing containers or immediately packed into hard gelatine capsules while gassing with nitrogen. Instead of hard gelatine capsules, soft gelatine capsules can also be used.

EXAMPLE 2

Powdered, freeze-dried tea leaves produced according to Example 1 are, for caffeine extraction with super-critical $CO_2$, extracted at a temperature of about 40° C. and a pressure of about 200 bar. After separating off the extracted caffeine, the $CO_2$ is recycled by decompression to below the critical point and, after renewed adjustment of the extraction conditions, the manner of working is repeated until the residual content of caffeine has decreased to below 5% of the initial value. The extracted tea powder is gassed with nitrogen until the carbon dioxide evolution from the plant material has ended and then, with continuation of the nitrogen gassing, packed into capsules as described in Example 1.

| | Bibliography |
|---|---|
| Lit. 1 | Scavenging effect of extracts of green tea and natural antioxidants on active oxygen radicals, Baoulu Z., Xiyojie L., Rungen H., Shujun Ch. and Xin W., Cell Biophysics, 1989, 14; 175–182 |
| Lit. 2 | Anticarcinogenic activity of green tea polyphenols, Komori A. et al., Jpn. J. Clin. Oncol. 1993, June 23 (3); 186–190 |
| Lit. 3 | A pilot study of Japanese green tea as a medicament: Antibacter.ial and Bactericidal effects, Naoki H., Yoshinori M, Masato I., Toru N. and Hiroshi N.J., Endodontics, 1991 17 (3): 122–24 |
| Lit. 4 | Effect of green tea catechins ori plasma cholesterol level in cholesterol-fed rats, Muramatsu K., Fukuyo M. and Hara Y., J. Nutr. Sci. Vitaminol. 1986, 32, 613–622 |
| Lit. 5 | DE 43 34 734 Al<br>GB 13 29 612<br>NL 68 09 368<br>Dalgleish J. McN.: Freeze-drying for the food industries, Elsevier Applied Science, 1990, pp. 68/59. |

SUMMARY

The invention concerns a process for the production of a preparation which contains the polyphenols of green tea (*Thea chinensis*) in readily available, non-oxidised form, characterised in that one cools fresh green tea leaves until the activity of the phenol oxidases contained therein has decreased to at most 1% of the value at normal temperature and simultaneously or immediately thereafter removes the water effective as reaction medium and products prepared according to this process.

I claim:

1. A process for producing a pulverized green tea leaf preparation which contains non-oxidized polyphenols normally found in green tea in a readily available form, comprising the steps of:

(a) cooling fresh green tea leaves until any activity of phenol oxidase contained therein has decreased to no more than 1% of the activity of said phenol oxidase in the fresh green tea leaves at ambient temperature, to form a cooled fresh green tea leaf preparation;

(b) dehydrating the cooled fresh green tea leaf preparation by removing any residual water contained therein simultaneously with or immediately after step (a) thereby reducing phenol oxidase activity and forming a cooled and dried green tea leaf preparation;

(c) pulverizing the cooled and dried green tea leaf preparation obtained in step (b) under non-oxidizing conditions to provide a pulverized dried green tea leaf powder, and;

(d) packing the dried green tea leaf powder obtained in step (c) under non-oxidizing and water-free conditions.

2. The process according to claim 1, wherein steps (a) and (b) are carried out simultaneously by lyophilisation.

3. The process according to claim 1, wherein steps (a)–(d) are carried out in a non-oxidizing atmosphere.

4. The process according to claim 1, wherein steps (a)–(d) are carried out under a nitrogen or noble gas atmosphere.

5. The process according to claim 1, wherein step (d) comprises packing the green tea leaf powder into biocompatible capsules in a non-oxidizing atmosphere, said capsules being characterized as being soluble in water having a temperature of about 100° C.

6. The process according to claim 5, further comprising adding edible antioxidants, vitamins, trace elements, or a combination thereof to the green tea leaf powder.

7. The process according to claim 5, further comprising adding to the green tea leaf powder flavor-affecting water-free aromas, derived from plants.

8. The process according to claim 7, wherein said plants are tea producing plants.

9. The process according to claim 1, further comprising extracting caffeine from the green tea leaf powder obtained in step (c).

10. The process according to claim 9, further comprising said step of extracting caffeine includes extracting the caffeine with supercritical $CO_2$.

11. A capsule comprising a powdered form of freeze-dried fresh green tea leaf, obtained by the process according to claim 1.

* * * * *